United States Patent [19]

Lankinen

[11] Patent Number: 4,940,051
[45] Date of Patent: Jul. 10, 1990

[54] INHALATION DEVICE
[75] Inventor: Tapio Lankinen, Turku, Finland
[73] Assignee: Huhtamki Oy, Turku, Finland
[21] Appl. No.: 777,085
[22] PCT Filed: Dec. 21, 1984
[86] PCT No.: PCT/FI84/00100
§ 371 Date: Aug. 26, 1985
§ 102(e) Date: Aug. 26, 1985
[87] PCT Pub. No.: WO85/02778
PCT Pub. Date: Jul. 4, 1985
[30] Foreign Application Priority Data
Dec. 28, 1983 [FI] Finland .................. 834816
[51] Int. Cl.⁵ .......................................... A61M 11/00
[52] U.S. Cl. ...................... 128/200.18; 128/200.23; 128/203.15
[58] Field of Search ...................... 128/200.23, 203.15, 128/203.16, 200.18, 200.14, 200.17, 200.22; 604/57, 58; 222/635, 190, 195; 239/338; 231/337

[56] References Cited

U.S. PATENT DOCUMENTS

| 2,501,279 | 3/1950 | Kark | 604/58 |
|---|---|---|---|
| 2,709,577 | 5/1955 | Pohndorf et al. | 239/338 |
| 2,865,370 | 12/1958 | Gattone | 128/200.23 |
| 3,045,671 | 7/1962 | Updegraff | 128/205.21 |
| 3,236,458 | 2/1966 | Ramis | 128/200.23 |
| 3,264,683 | 8/1966 | Lloyd | 239/338 |
| 3,522,806 | 8/1970 | Szekely | 128/200.18 |
| 3,744,681 | 7/1973 | Morane | 128/200.18 |
| 3,809,084 | 5/1974 | Hansen | 222/190 |
| 3,838,686 | 10/1974 | Szekely | 128/200.18 |
| 3,864,326 | 2/1975 | Babington | 239/337 |
| 4,150,071 | 4/1979 | Pecina | 739/338 |
| 4,228,795 | 10/1980 | Babington | 128/200.22 |
| 4,470,412 | 9/1984 | Nowacki | 128/200.18 |

FOREIGN PATENT DOCUMENTS

| 452438 | 11/1948 | Canada | 128/200.18 |
|---|---|---|---|
| 0009667 | 4/1980 | European Pat. Off. | 128/200.23 |
| 0045419 | 2/1982 | European Pat. Off. | 128/200.23 |
| 296194 | 5/1916 | Fed. Rep. of Germany | 239/338 |
| 1046264 | 6/1959 | Fed. Rep. of Germany | |
| 570958 | 2/1928 | France | 239/338 |
| 134730 | 12/1976 | Norway | |
| 332914 | 2/1976 | Sweden | |
| 415957 | 3/1981 | Sweden | |
| 65826 | 9/1913 | Switzerland | 239/338 |
| 623955 | 5/1949 | United Kingdom | 239/338 |
| 958867 | 5/1964 | United Kingdom | 239/338 |
| 975754 | 11/1964 | United Kingdom | 128/200.23 |
| 2000555 | 1/1979 | United Kingdom | 128/200.23 |

Primary Examiner—Max Hindenburg
Assistant Examiner—K. M. Reichle
Attorney, Agent, or Firm—Howard M. Ellis; Michael L. Dunn

[57] ABSTRACT

The invention relates to an inhalation device comprising a socket (1) intended for an aerosol container (3) of a medicament to be inhaled, the bottom of the socket being fitted with a baffle (6) which receives a valve stem (4) fixed to a container (3) and penetrates into an inhalation chamber (10) provided with a mouthpiece (11), and a nozzle (8) at the end of an inlet duct (7) terminating in the inhalation chamber (10). Mounted at a distance from the nozzle (8) of inlet duct (7), the nozzle being directed towards the end of inhalation chamber (10) remote from mouthpiece (11), is an opposing baffle plate (9) for pulverizing a spray of the medicament in inhalation chamber (10). The inhalation chamber (10) is provided with a one-way valve (5) for passing air into chamber (10).

13 Claims, 3 Drawing Sheets

INHALATION DEVICE

BACKGROUND OF THE INVENTION

The present invention relates to an inhalation device provided with a socket for an aerosol container that contains material to be inhaled, the bottom of said socket being fitted with a baffle which receives the valve stem of said container and extends into an inhalation chamber provided with a mouthpiece, and a nozzle mounted on the end of an inlet channel and terminating in said inhalation chamber.

At present, medicine is inhaled into the lungs by using either an inhalation aerosol or a powder metering device. A major drawback in using a inhalation aerosol device is that the dosing must be effected in the beginning of inhalation, which all patients cannot manage. Another minor drawback is that aerosol does not work at temperature below zero due to the relatively low vapor pressure of the generally used propellant compositions.

Powder metering devices do not suffer from the above drawbacks but, due to the small amounts of medicine used, they require the use of a carrier, at present lactose or glucose. These are hygroscopic carbohydrates which readily adhere to a moist surface. A powder metering device gets wet on the inside if exhaled through or brought from cold weather to warm indoor air. A conseuence is soiling of the device and diminishing of the inhaled dosage. An inexact dosage may also result if an inhalation-ready device is held in a wrong position wherever some of the powder falls out through the inhalation hole. From a user's point of view, filling of a powder metering device with a medical formulation for each dosage is inconvenient.

Lactose and glucose are useful as carriers for the mount pathogenes but there is no doubt that decay of the teeth will increase because of the continuous exposure to the sugar caused by the powder. Also, for patients who are-over-sensitive to lactose, such a medical formulation is not always suitable.

SUMMARY OF THE INVENTION

An object of the invention is to provide an inhalation device whereby all the above drawbacks are eliminated, i.e. a device that is simple to operate and provides effective inhalation of the substance to be inhaled with procedures as simple as possible.

The above object of the invention is fulfilled with a device characterized by an opposing baffle plate for pulverizing the medicine spray in the inhalation chamber mounted at a distance from the inlet nozzle which is directed towards the end opposite of the inhalation chamber mouthpiece, and a one-way valve for passing air into the chamber.

Thus, the above device comprises a combination of an aerosol spray and a powder inhalation device. In the device, the dosage of a powdered medical formulation proceeds from an aerosol container. This arrangement is highly preferable and simple from the point of view of a user but still permits the inhalation of a powder to proceed according to the user's own inhaling. After all, this type of inhalation has been found more effective than the delivery of an aerosol spray directly into the mouth.

The air needed for inhalation is passed into the inhalation chamber through a one-way valve, preferably mounted on the wall between the socket and the inhalation chamber. The one-way valve receives the best possible protection in this position below the aerosol container. Also, the socket is usually fitted with a protective cover.

For the best possible spray atomization, said baffle plate is concave with repect to the nozzle. Thus, the spray atomizes effectively and spreads all over the chamber.

The invention will now be described in more detail with reference made to the accompanying drawings, in which FIG. 1 shows one embodiment of a device of the invention;

DETAILED DESCRIPTION OF THE INVENTION

Figure 1:
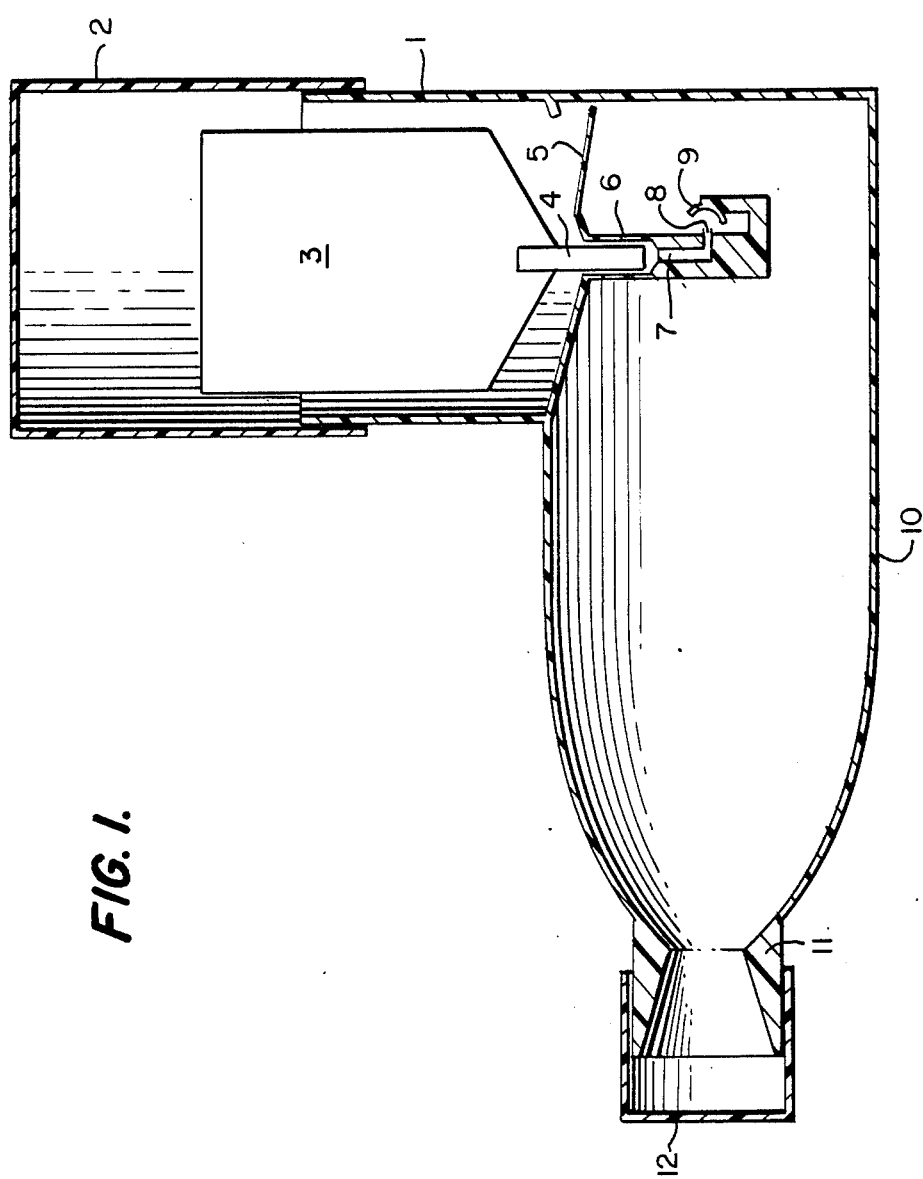

A device shown in FIG. 1 comprises a tubular body for forming an inhalation chamber 10 with an upright socket 1 at the end. This socket 1 is intended for an aerosol container 3 containing a medical formulation. The bottom of said socket is fitted with a baffle member 6 provided with a channel whose inlet is sufficiently wide to recieve a valve stem 4 fixed to the aerosol container 3 inserted therein. Valve stem 4 engages with a narrowed portion of the channel below the widened valve stem inlet. The channel continues as a narrow duct 7 lenthwise within said baffle member 6. The end of this duct 7 is provided with a cross-channel, extending crosswise with respect to the longitudinal direction of said duct and terminating in a nozzle member 8.

Spaced from and opposite to this nozzle 8 is mounted a baffle plate 9 whose surface is concave with respect to nozzle 8.

The socket 1 for receiving the aerosol container 3 is open and provided with a protective cap 2 for covering said aerosol container 3.

The wall between inhalation chamber 10, formed by the body and socket 1 is provided with a one-way valve 5 which only opens towards the inhalation chamber so as to facilitate the passage of air into the inhalation chamber. An air-flow in the opposite direction closes said valve 5.

The inhalation chamber is an elongated tubular body, whose end remote from socket 1 is fitted with a mouthpiece 11 to be positioned in or in front of the mouth of a user and coverable with a protective cap 12.

The device is operated as follows. The aerosol container 3 filled with a medical formulation is positioned in socket 1 and valve stem 4 of the container is pushed down to the bottom of the channel in baffel member 6. Pressing said aerosol container 3 still further down serves to open a metering valve and a certain amount of gas and medicament suspension discharges into duct 7 and out of its nozzle 8 rushing towards baffle plate 9. This deflects the expandable mixture into the inhalation chamber. The expansion begins in the rear section of inhalation chamber 10 and the expanding gas drives the air in front of it towards said mouthpiece. During the expansion period, said one-way valve 5 prevents the discharge of gas from chamber 10. The released amount of gas is such that, at normal pressure, it only fills a part of the inhalation chamber. Medicament particles form a mixture together with the gas from valve 5. When a user positions the open mouthpiece 11 in his or her mouth and inhales, said one-way valve 5 opens and air flows therethrough into inhalation chamber 10. The flowing air picks up the powdered medicament in the chamber carrying it into the lungs of a user.

As a result of the operating principle, the propellant pressure and the size of the nozzle orifice are not critical in a device of the invention the same way as in a normal aerosol device. By increasing gas pressure, the device will operate at temperatures below zero. The size of the nozzle orifice determines the time needed for expansion so that as much medicament as possible is inhaled.

As shown in figures, the device is provided with a container protection cap 2 for protecting the device and especially said aerosol container 3 during transport. In addition, mouthpiece 11 is closed by means of a protective cap 12 making the device totally sealed and covered during transport to avoid contamination.

Figure 2:
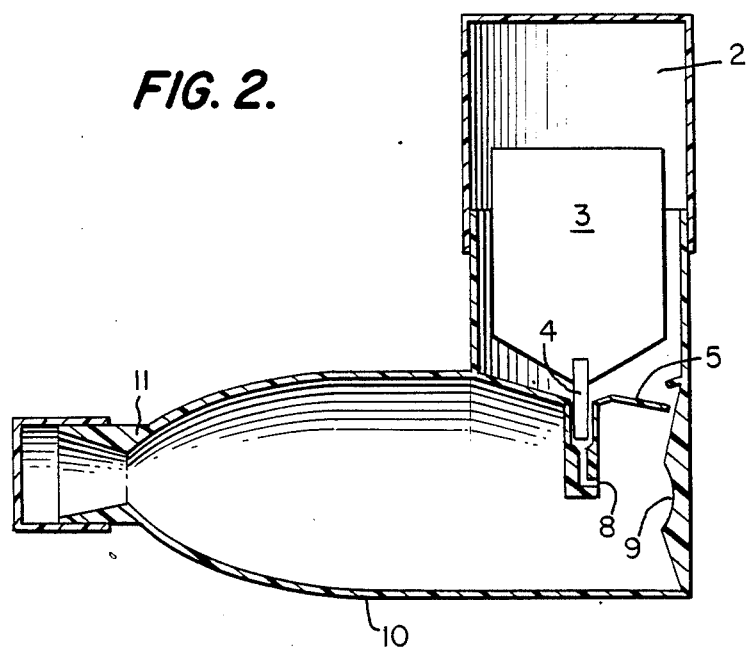
FIGS. 2-3 show different modifications of such device.
Figure 3:
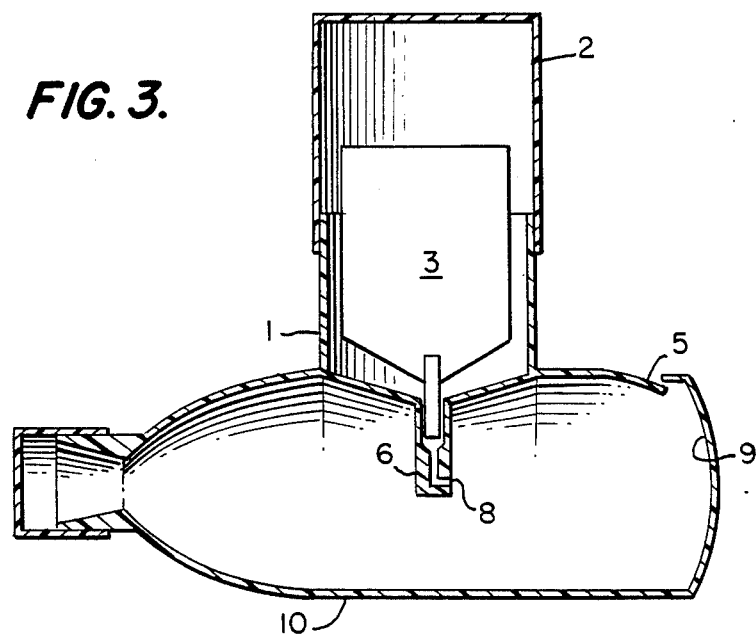
Figure 4:
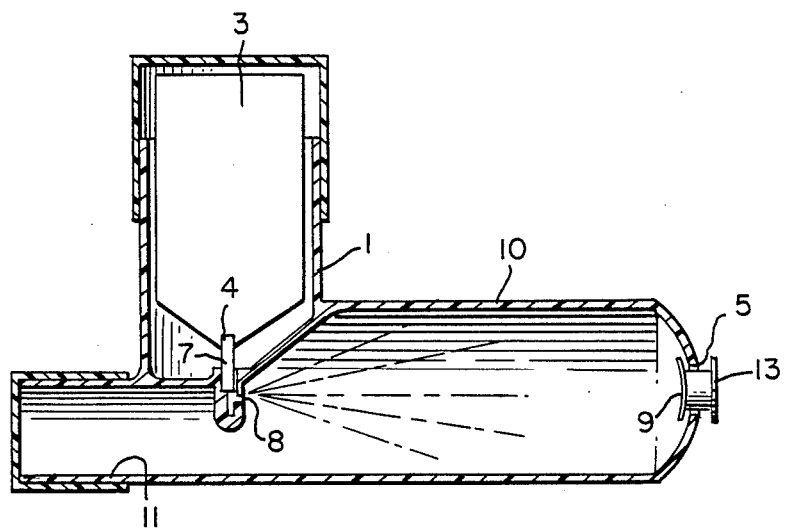
FIG. 4 shows an alternative embodiment of such device with the aerosol container positioned adjacent to the mouthpiece.

FIGS. 2-4 illustrate various embodiments of the device shown in FIG. 1. The embodiments shown in these figures include the same components as FIG. 1. Therefore, the embodiments shown in these figures are not described in detail with the basic design being the same as in FIG. 1.

In the embodiment shown in FIG. 2, a concave baffle plate is mounted on the end wall of inhalation chamber 10. Thus, the end wall can be provided with a separate baffle plate 9 or the end wall itself can be designed as a concave baffle plate 9, as shown in FIG. 3. In the case depicted in FIG. 3, said socket 1 together with its baffle 6, for said aerosol container 3 is positioned in the midsection of inhalation chamber, the distance between nozzle 8 and baffle plate 9 being relatively long. A one-way valve 5 is mounted adjacent to baffle plate or surface 9.

In the embodiment shown in FIG. 4, said socket 1 for aerosol container 3 is positioned in the forward end of a device adjacent to mouthpiece 11 of inhalation chamber 10. Chamber 10 is designed to have a tubular shape and its end remote from mouthpiece 11 is rounded. This end is provided with a hole with a shut-off member inserted therein. This shut-off member 13 comprises a component penetrating into inhalation chamber 10 and having a concave surface to provide the baffle plate of the invention. Baffle plate 9 is dimensioned so as to totally cover said hole of inhalation chamber 10. During the spraying action, a spray of medicament discharges charges from nozzle 8 rearwards and towards the baffle plate, urging the latter against the hole and closing off said chamber 10. During the inhaling, said shut-off member 13 can be pressed inwards in the hole and stopper lugs outside said shut-off member prevent the member from penetrating completely into the inhalation chamber. At the same time, however, replacement air is allowed to pass through the hole into the inhalation chamber. Thus, said shut-off member 13 operates as a one-way valve 5.

I claim:

1. An inhalation device which comprises a tubular body defining an inhalation chamber, said tubular body having a sidewall, an endwall disposed at one end of said tubular body and a mouthpiece at the opposing end of said body, said sidewall having mounting means for mounting a container of medicament and conduit means for providing a medicament passageway from said mounting means to said inhalation chamber and for discharging medicament into said chamber in a direction toward said endwall, said device including means for deflecting medicament discharged by said conduit means in a direction towards said mouthpiece, and valve means for introducing air into said chamber during inhalation.

2. The apparatus of claim 1 wherein the means for mounting a container of medicament comprises means for mounting an aerosol container.

3. The device claim 2 wherein the means for deflecting is a baffle plate positioned in the inhalation chamber generally in the region of the endwall of said tubular body.

4. The device claim 3 wherein said conduit means includes nozzle means for directing the medicament towards said baffle plate positioned generally in the region of the endwall of said tubular body.

5. The device of claim 4 wherein the baffle plate has a generally concave configuration facing the nozzle means.

6. The device of claim 5 wherein said generally concave shaped baffle plate is disposed in the inhalation chamber between the nozzle means and endwall of said tubular body.

7. The device of claim 5 wherein said generally concave shaped baffle plate is disposed in the inhalation chamber adjacent to the endwall of the tubular body.

8. The device of claim 5 wherein the endwall of the tubular body is the generally concave shaped baffle plate.

9. The device of claim 5 wherein the valve means is a one-way valve for introducing air into the inhalation chamber, said valve being mounted in the sidewall of the tubular body.

10. The device of claim 9 wherein the one-way air valve is positioned in the sidewall adjacent to the mounting means for the aerosol container.

11. The device of claim 5 wherein the valve means is a one-way valve for introducing air into the inhalation chamber, said valve being mounted in the endwall of said tubular body.

12. The device of claim 5 wherein the generally concave shaped baffle plate is affixed to the conduit means.

13. An inhalation device which comprises a generally elongated tubular enclosure defining an inhalation chamber, said enclosure having an elongated sidewall, an endwall disposed at one end of said enclosure and a mouthpiece at the opposing end of said enclosure, said device including means for mounting an aerosol container, conduit means with nozzle means for conducting container contents to said inhalation chamber and for discharging said container contents into said chamber in a direction toward said endwall, said enclosure having baffle means positioned between the enclosure endwall and the nozzle means for dispersing the container contents discharged by said nozzle means in a direction towards said mouthpiece, said device including valve means for introducing air from outside said enclosure into said chamber during inhalation.

* * * * *